United States Patent
Zenoni et al.

(10) Patent No.: US 7,964,589 B2
(45) Date of Patent: *Jun. 21, 2011

(54) INJECTABLE STERILE PHARMACEUTICAL FORMULATION CONTAINING AT LEAST TWO ACTIVE PRINCIPLES

(75) Inventors: Maurizio Zenoni, Paullo (IT); Angelo Giovanni Cattaneo, Monte Marenzo (IT); Leonardo Marsili, Brescia (IT)

(73) Assignee: ACS Dobfar S.p.A., Tribiano (IT)

(*) Notice: Subject to any disclaimer, the term of this patent is extended or adjusted under 35 U.S.C. 154(b) by 1301 days.

This patent is subject to a terminal disclaimer.

(21) Appl. No.: 11/493,522

(22) Filed: Jul. 27, 2006

(65) Prior Publication Data

US 2007/0054889 A1 Mar. 8, 2007

(30) Foreign Application Priority Data

Sep. 2, 2005 (IT) .............. MI2005A1630

(51) Int. Cl.
*A61K 31/43* (2006.01)
*A61K 31/70* (2006.01)
*A01N 43/04* (2006.01)
(52) U.S. Cl. .......................... 514/196; 514/36
(58) Field of Classification Search ................... 514/196
See application file for complete search history.

(56) References Cited

U.S. PATENT DOCUMENTS 4,344,955 A * 8/1982 Niemers et al. ............... 514/194
5,559,241 A * 9/1996 Corsi et al. .................... 548/178

FOREIGN PATENT DOCUMENTS

EP 1 468 697 A1 10/2004
WO WO 2004/098643 A1 11/2004

OTHER PUBLICATIONS

Arzuaga et al. Quantitation and stability of piperacillin and tazobactam in plasma and ultrafiltrate from patients undergoing continuous venovenous hemofiltration by HPLC. Biomedical Chromatography. vol. 19, Issue 8, pp. 570-578, Apr. 12, 2005.*
M. Pfaller et al., Relative Efficacy of Tazobactam, Sulbactam and Clavulanic Acid in Enhancing the Potency of Ampicillin Against Clinical Isolates of Enterobacteriaceae, Eur. J. Clin. Microbiol. Infect. Dis., pp. 200-205.

* cited by examiner

*Primary Examiner* — Sreeni Padmanabhan
*Assistant Examiner* — Layla Soroush
(74) *Attorney, Agent, or Firm* — Oblon, Spivak, McClelland, Maier & Neustadt, L.L.P.

(57) ABSTRACT

Mixtures of at least two active principles, of which at least one is the sodium salt, are precipitated from an organic solution containing the same active principles in salified or non-salified acid form.

4 Claims, No Drawings

INJECTABLE STERILE PHARMACEUTICAL FORMULATION CONTAINING AT LEAST TWO ACTIVE PRINCIPLES

BACKGROUND OF THE INVENTION

1. Field of the Invention

The most widely used antibiotics are undoubtedly those pertaining to the class of beta-lactams. It has been known for many years that when these antibiotics are used in clinical therapy their "in vivo" effectiveness progressively diminishes because of beta-lactamase enzymes capable of degrading the beta-lactam ring. Fortunately, the discovery of certain substances able to inhibit the activity of the aforesaid enzymes has enabled certain beta-lactam antibiotics, ineffective if used alone, to be still used by bringing them into association with the said inhibitors. These antibiotics include piperacillin, which is administered by injection as the sodium salt. Following the decay of its therapeutic effectiveness for the aforesaid reason, piperacillin was associated with tazobactam sodium.

2. Discussion of the Related Art

Piperacillin sodium is normally prepared by lyophilization, the very soft lyophilizate obtained ensuring rapid solubilization, as described in U.S. Pat. No. 4,477,452 and U.S. Pat. No. 4,534,977. It is therefore evident that the lyophilization of piperacillin or of an association in which it is present in a prevalent percentage is little productive, precisely because the operation has to be carried out in very dilute solution. On the other hand, mixing piperacillin sodium with separately lyophilized tazobactam sodium presents a problem caused by the different densities of the two components: in this respect, in the mixture a non-homogeneous distribution of the powders occurs in the sense that the tazobactam sodium, of greater density than piperacillin sodium, tends to separate within the lower layers of the mixture.

U.S. Pat. No. 5,763,603 claims a crystalline sodium salt of tazobactam, but even using this crystalline salt the problem of homogeneity of the mechanical mixture of the piperacillin and tazobactam sodium salts can evidently not be solved because of the low density of lyophilized piperacillin sodium.

This fact evidently means that piperacillin sodium and tazobactam sodium mixtures cannot be prepared in quantities greater than those of a single injectable dose.

SUMMARY OF THE INVENTION

For the type of problem described, which can be totally general and not limited to the piperacillin sodium+tazobactam sodium association, a solution has finally been found by the present inventors, who have surprisingly discovered that a pharmaceutical formulation can be prepared containing the active principles in salified form and precipitated under sterile conditions, hence not in aqueous solution, but perfectly soluble in water and possessing maximum stability. The solid sterile pharmaceutical formulation according to the invention is formed from at least two active principles, of which at least one is salified with a sodium salt chosen from the group consisting of sodium carbonate, sodium 2-ethyl-hexanoate, sodium acetate, sodium citrate, sodium lactate, sodium methylate, sodium ethylate.

This formulation is obtained by a process according to which at least one active principle is dissolved in acid form, at a temperature between −10° C. and +25° C., in a solvent consisting of at least one chosen from the group consisting of water, acetone, methanol, ethanol, then salifying the mixture by adding suitable sodium salts chosen from the group consisting of sodium carbonate, sodium 2-ethyl-hexanoate, sodium acetate, sodium citrate, sodium lactate, sodium methylate, sodium ethylate, sterilely filtering the solution obtained, precipitating the salified mixture by feeding the sterile solution dropwise into at least one organic solvent chosen from the group consisting of isopropyl alcohol, ethyl alcohol, methyl acetate, ethyl acetate, acetone, methylene chloride at a temperature between 0° C. and 50° C., filtering the saline mixture obtained and finally drying it under vacuum at a temperature between 20° C. and 75° C.

It is not necessary that precipitation of the active principles is effected simultaneously, but only that it takes place in the same reactor, even at successive moments. In the case of the piperacillin+tazobactam association, the product obtained is amorphous and stable, and appears and behaves as if consists of a single component, enabling it to be packaged without distinction in single or multiple dosages without the problems caused by density differences between the individual components.

DETAILED DESCRIPTION OF THE INVENTION

Example 1

7 g sodium 2-ethylhexanoate are dissolved in a mixture of 17 ml water and 30 ml methanol cooled to 0° C. 20 g acid piperacillin monohydrate are then added and the mixture maintained under stirring until complete dissolution. 1.5 g sodium 2-ethylhexanoate are added followed by 2.5 g tazobactam acid. The mixture is maintained under stirring for 90 min between 0° C. and +5° C., the suspension obtained is filtered and, while maintaining at the same temperature, is fed dropwise over at least 30 min into 400 ml isopropyl alcohol maintained at 35° C. Agitation is continued for 30 min at 35° C., the mixture filtered, the product washed with isopropyl alcohol and dried under vacuum at 75° C. for 24 h.
18.6 g are obtained with the following analytical data:
piperacillin sodium equivalent to 14.47 g of acid;
tazobactam sodium equivalent to 1.73 g of acid;
K.F.: 3.5%.
isopropyl alcohol: substantially absent
pH of reconstituted aqueous solution: 5.6.

Example 2

6.9 g sodium 2-ethylhexanoate are dissolved in a mixture of 20 ml water and 20 ml methanol cooled to 0° C. 20 g acid piperacillin monohydrate are then added and the mixture maintained under stirring until complete dissolution. 2.5 g tazobactam acid are added followed by 1.5 g sodium 2-ethylhexanoate. The walls of the reaction flask are washed with 10 ml methanol at 0° C. The mixture is maintained under agitation for 90 min between 0° C. and +5° C., the solution obtained is filtered and, while maintaining it at the same temperature, is fed dropwise over 45 min into 400 ml isopropyl alcohol maintained at 35° C. Stirring is continued for 30 min at 35° C., the mixture cooled to +15° C. and stirred for 30 min. It is filtered, the product washed with 30 ml isopropyl alcohol and dried under vacuum at 70° C. for 90 min.
18.6 g are obtained with the following analytical data:
piperacillin sodium equivalent to 14.47 g of acid;
tazobactam sodium equivalent to 1.73 g of acid;
K.F.: 3.5%.
isopropyl alcohol: substantially absent
pH of reconstituted aqueous solution: 5.6.

What we claim is:

1. A process for preparing a formulation comprising the two active principles piperacillin and tazobactam:
   wherein the process comprises:
   adding a first of the two active principles in acid form, at a temperature between −10° C. and +25° C., in a solvent to obtain a mixture;
   salifying the mixture by adding at least one suitable sodium salt to obtain a solution;
   adding the second active principle into the solution of the first active principle added in acid form;
   preparing a solution mixture of the active principles;
   sterilely filtering the solution mixture obtained,
   feeding the sterile filtered salified solution dropwise into at least one organic solvent at a temperature between 0° C. and 50° C. to precipitate a saline solid mixture;
   filtering the precipitated saline mixture obtained; and
   drying the filtered precipitated saline mixture under vacuum at a temperature between 20° C. and 75° C.;
   wherein
   the solvent for dissolving the active principles is at least one selected from the group consisting of water, acetone, methanol and ethanol,
   the at least one suitable sodium salt for salifying the mixture is at least one selected from the group consisting of sodium carbonate, sodium 2-ethyl-hexanoate, sodium acetate, sodium citrate, sodium lactate, sodium methylate, and sodium ethylate, and
   the at least one organic solvent into which the sterile solution is fed is at least one selected from the group consisting of isopropyl alcohol, ethyl alcohol, methyl acetate, ethyl acetate and acetone.

2. The process according to claim 1, further comprising:
   adding the second active principle as a solution of a pharmaceutically acceptable salt of an organic base.

3. The process according to claim 2, wherein the pharmaceutically acceptable base is trimethylamine, lysine, arginine or a mixture thereof.

4. A process for preparing a solid sterile pharmaceutical formulation comprising the two pharmaceutically active principles piperacillin and tazobactam:
   wherein the process comprises:
   adding piperacillin in acid form, at a temperature between −10° C. and +25° C., into a solvent to obtain a mixture;
   salifying the mixture by adding at least one suitable sodium salt to obtain a solution;
   adding tazobactam into the solution;
   preparing a solution mixture of the salified solution of piperacillin and tazobactam;
   sterilely filtering the solution mixture obtained,
   feeding the sterilely filtered solution mixture dropwise into at least one organic solvent at a temperature between 0° C. and 50° C. to precipitate a saline solid mixture;
   filtering the precipitated saline solid mixture obtained; and
   drying the filtered precipitated saline solid mixture under vacuum at a temperature between 20° C. and 75° C.;
   wherein
   the solvent for dissolving piperacillin in acid form and tazobactam is at least one selected from the group consisting of water, acetone, methanol and ethanol,
   the at least one suitable sodium salt for salifying the mixture is at least one selected from the group consisting of sodium carbonate, sodium 2-ethyl-hexanoate, sodium acetate, sodium citrate, sodium lactate, sodium methylate, and sodium ethylate, and
   the at least one organic solvent into which the sterile filtered solution is fed is at least one selected from the group consisting of isopropyl alcohol, ethyl alcohol, methyl acetate, ethyl acetate and acetone.

* * * * *